United States Patent [19]

Umezawa et al.

[11] 4,238,507
[45] Dec. 9, 1980

[54] PHARMACOLOGICAL COMPOUND WITH IMMUNOPOTENTIATING ACTIVITY AND PRODUCTION AND USES THEREOF

[75] Inventors: Hamao Umezawa; Tomio Takeuchi, both of Tokyo; Takaaki Aoyagi, Fujisawa; Masaaki Ishizuka, Tokyo; Hajime Morishima, Tokyo; Ikuo Matsumoto, Tokyo; Takuzo Yamamoto, Tokyo, all of Japan

[73] Assignee: Zaidan Hojin Biseibutsu Kagaku Kenkyu Kai, Tokyo, Japan

[21] Appl. No.: 21,222

[22] Filed: Mar. 16, 1979

[51] Int. Cl.³ .................... A01N 37/12; C07C 101/72
[52] U.S. Cl. ................................... 424/319; 562/444; 260/465 E; 260/340.7
[58] Field of Search ..................... 562/444, 445, 446; 560/39, 40; 424/319

[56] References Cited

U.S. PATENT DOCUMENTS

| | | | |
|---|---|---|---|
| 3,395,176 | 7/1968 | Sletzinger et al. | 562/446 |
| 3,801,601 | 4/1974 | Reinhold et al. | 562/446 |
| 3,825,590 | 7/1974 | Suh et al. | 562/444 |
| 3,891,634 | 6/1975 | Dunn | 562/444 |

Primary Examiner—James H. Reamer
Attorney, Agent, or Firm—Larson, Taylor and Hinds

[57] ABSTRACT

A new compound having the formula

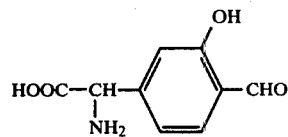

and now designated forphenicinol is produced, which exhibits an immunopotentiating activity. This new compound as well as its pharmaceutically acceptable salts and hydrates are useful for immunotherapy and treatment of immune diseases and disorders in living animals, including human beings. The new compound can be produced by hydrolysis of the corresponding aminonitrile compound of the formula

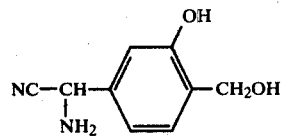

or by reduction of forphenicine.

4 Claims, No Drawings

PHARMACOLOGICAL COMPOUND WITH IMMUNOPOTENTIATING ACTIVITY AND PRODUCTION AND USES THEREOF

SUMMARY OF THE INVENTION

Field of the Invention

This invention relates to a new compound now denominated forphenicinol and having immunopotentiating properties, to processes for the production thereof and to uses thereof as immunopotentiator or for enhancing immunological response in animals and humans.

BACKGROUND OF THE INVENTION

We have studied in search of useful derivatives of a known compound, forphenicine having the following structure:

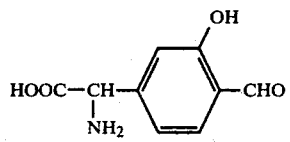

Forphenicine is a known substance which was first isolated from the culture broth of a strain of actinomycetes by H. Umezawa et al. and which is useful as a strong inhibitor of alkaline phosphatase (Japanese patent application pre-publication "Kokai" No. 116685/75, Journal of Antibiotics Vol. 31, No. 3, pp. 244–246 and Vol. 31, No. 5, pp. 483–484 (1978)).

As a result of our extensive studies, we have now succeeded in producing a new compound of the structural formula:

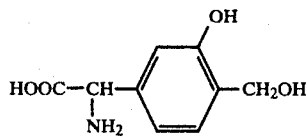

and its salts and hydrates. We have further found that these compounds have immunopotentiating activity and are thus useful as an immunopotentiator for enhancing the immune response in living animals and humans. It is also found that the new compound (I) of this invention is more stable than forphenicine and upon oral administration exhibits a higher activity than forphenicine.

An object of this invention is to provide new compounds which exhibit immunopotentiating activities. Another object of the invention is to provide processes of producing these new, useful compounds. Further object of the invention is to provide an immunopotentiator comprising these compounds.

Other objects and utilities of the invention will become apparent from the following descriptions.

DETAILED DESCRIPTION OF THE INVENTION

According to a first aspect of this invention, therefore, there is provided a new compound of the structural formula:

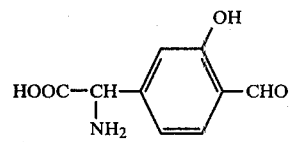

and its pharmaceutically acceptable salts and hydrates and salts thereof.

The compound of formula (I), which is referred to as forphenicinol, is in the form of colorless crystals which gradually decompose above 200° C. with discoloration to brown.

The compound (I) is of amphoteric nature, so that it may form a great number of salts with various acids and bases. The pharmaceutically acceptable salts of the compound (I) according to this invention include salts with an inorganic acid such as hydrochloric acid, sulfuric acid and the like; with an organic acid such as maleic, fumaric, tartaric benzenesulfonic and toluenesulfonic acids etc.; with an alkali metal such as sodium and potassium; with an alkaline earth metal such as calcium and magnesium; and with an organic amine such as trialkylamine, dicylohexylamine and the like.

The compound (I) may be prepared by a number of processes. Some examples of these processes may be diagrammatically shown by the following scheme, wherein $R_1$ represents an alkyl group and the group

represents a divalent hydroxyl-protecting group where $R_2$ and $R_3$ each represents hydrogen atom or an alkyl group.

Scheme

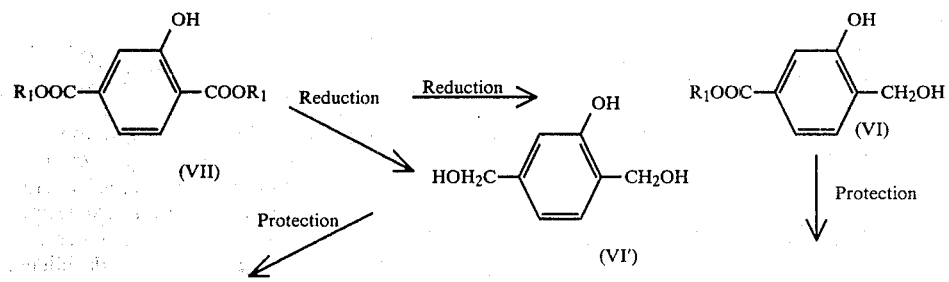

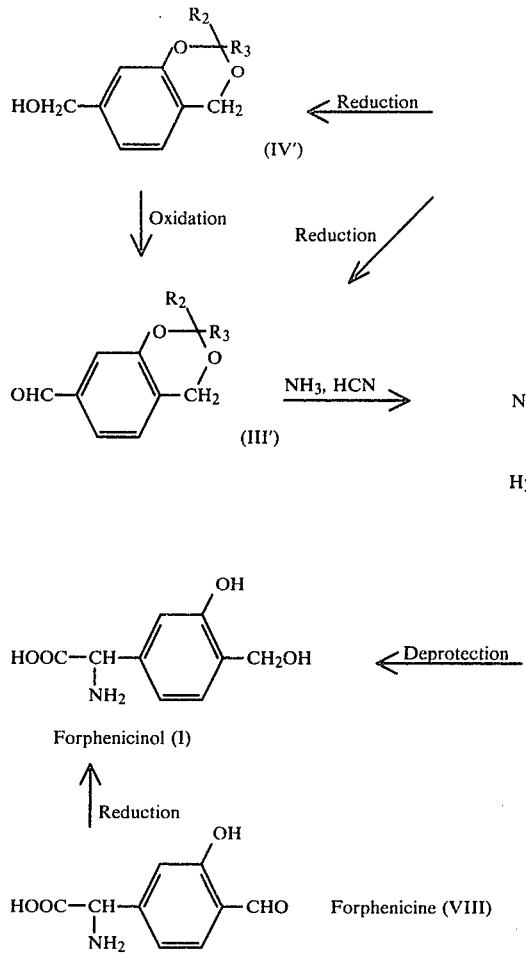

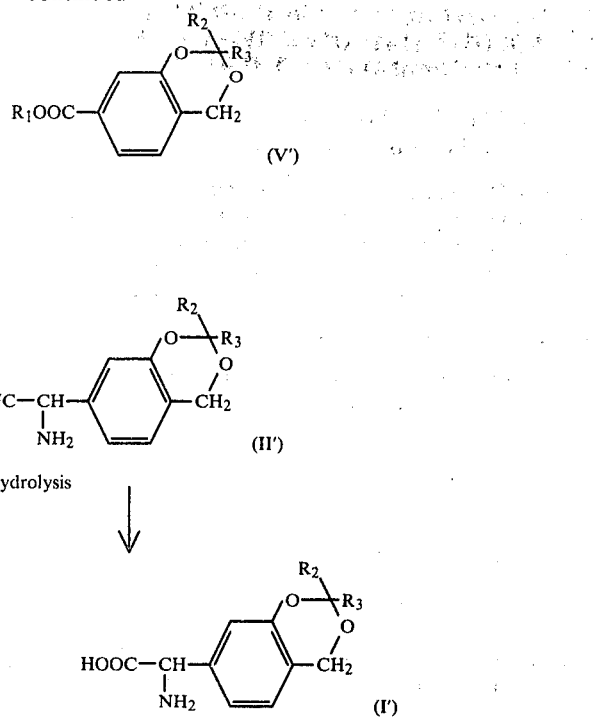

Forphenicinol (I)

Forphenicine (VIII)

In a second aspect of this invention, there is provided a process for the production of the compound of the above formula (I), which comprises hydrolizing an aminonitrile compound of the general formula:

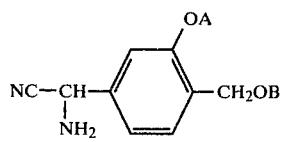

(II)

wherein A and B each represents hydrogen atom or a hydroxyl-protecting group, or A and B taken together form a divalent hydroxyl-protecting group, and then removing from the resulting hydrolysis product the protecting group or groups if remaining in the hydrolysis product.

The 3-hydroxyl group and 4-hydroxymethyl group of the starting aminonitrile compound (II) may or may not be blocked, although generally both of these groups are preferably blocked prior to the hydrolysis reaction. The protecting groups to be employed for this purpose may be any known hydroxyl-protecting group. Thus, the protecting groups for the 3-phenolic hydroxyl group include methyl, isopropyl, t-butyl, benzyl, methoxymethyl, tetrahydropyranyl, phenacyl, acetyl, benzoyl, methoxycarbonyl, ethoxycarbonyl, benzyloxycarbonyl, β, β, β-trichloroethoxycarbonyl, benzenesulfonyl and trimethylsilyl groups. The hydroxylprotecting groups for the 4-hydroxymethyl group include methyl, t-butyl propenyl, benzyl, trityl, substituted trityl, trimethylsilyl, tetrahydropyranyl, tetrahydrothiofuranyl, tetrahydrothiopyranyl, methoxytetrahydropyranyl, acetyl, benzoyl, para-nitrobenzoyl, formyl, trifluoroacetyl, chloroacetyl, methoxyacetyl, phenoxyacetyl, ethoxycarbonyl, methoxycarbonyl, isobutyloxycarbonyl, benzyloxycarbonyl, 2,2,2-trichloroethoxycarbonyl, para-nitrophenoxycarbonyl, phenylcarbamoyl, benzylthiocarbonyl, pivaloyl, 3-benzoylpropionyl, benzoylformyl, tigloyl, succinoyl, o-benzyloxycarbonylbenzoyl, 3-phenylpropionyl, nitro, tosyl and 2,4-dinitrobenzenesulfenyl groups.

The groups A and B taken together may form a divalent hydroxyl-protecting group which protects both the 3-phenolic hydroxyl group and the 4-hydroxymethyl group. The divalent protecting groups include a group of the formula:

in which $R_2$ and $R_3$ each represents hydrogen atom, an alkyl group, for example, containing 1 to 4 carbon atoms, notably methyl, ethyl, propyl, isopropyl or butyl group, or an aryl group, for example, phenyl, tolyl or p-methoxyphenyl group, and an example of which is an alkylidene group such as ethylidene and isopropylidene groups or an aralkylidene group such as benzylidene group; and a cycloalkylidene group of the formula

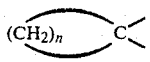

in which n is an integer of 4, 5 or 6, for example, cyclohexylidene group; and tetrahydropyranylidene group.

Specific examples of the divalent hydroxyl-protecting group include methylene, ethylidene, benzylidene, substituted benzylidene, isopropylidene, cyclohexylidene, cyclopentylidene, ethoxymethylene, methoxymethylene, methoxyethylidene and such a group which forms a cyclic carbonate of the formula

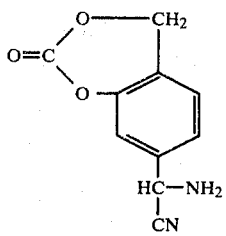

The particular hydroxyl-protecting group will be chosen with taking into consideration the conditions for the hydrolysis of the aminonitrile compound (II) and the stability of the object compound (I). It is preferred, however, to use a group which protects concurrently both the phenolic hydroxyl and the hydroxymethyl groups. For example, isopropylidene group is most preferred.

In the second aspect process of this invention, the hydrolysis reaction is generally carried out by treating the aminonitrile compound (II) with an acid or alkali in the presence of water. Typical examples of the acid for use in the reaction include hydrochloric, sulfuric and polyphosphoric acids and those of the alkali include an alkali metal hydroxide such as sodium and potassium hydroxides and an alkaline earth metal hydroxide such as calcium, magnesium and barium hydroxides. The reaction may be carried out in any known solvent, provided that it has no adverse effect on the reaction. Examples of the solvent to be used are water, methanol, ethanol, acetic acid, dioxane or mixtures thereof. The reaction usually may be effected at ambient temperature or at an elevated temperature though the reaction temperature is not critical.

By the hydrolysis, the nitrile group of the compound (II) may be converted into the form of carboxylic amido group. The acid amide precursor so obtained may be, if desired, isolated from the reaction mixture by a conventional technique. In most cases, however, the precursor is further hydrolized to give the hydrolysis product in the form of carboxylic acid or its corresponding carboxylate, without isolation.

When the hydroxyl-protecting group used is removable even under the predominating hydrolysis conditions, the object compound (I) can be directly produced. If the protecting group is not removable to remain in the hydrolysis product, then the object compound (I) can be obtained by subsequent removal of the protecting group from the hydrolysis product.

This invention also provides a process for the preparation of the aminonitrile compound (II) which is to be used as starting material in the process according to the second aspect of the invention.

The compound (II) may be prepared by oxidizing an alcohol compound of the formula:

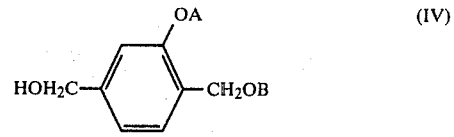

wherein A and B are as defined hereinabove, to produce a substituted benzaldehyde compound of the formula:

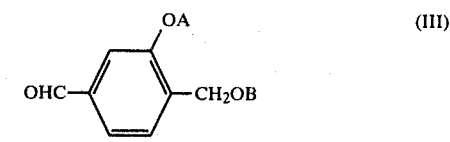

and reacting this benzaldehyde compound (III) with ammonia or an ammonium salt and hydrocyanic acid or a salt thereof.

The oxidizing agent to be used for the oxidation reaction may be any known one and includes, for example, activated manganese dioxide, chromic acid, lead tetraacetate, ruthenium tetraoxide, selenium dioxide, halogens and dimethylsulfoxide.

The reaction to convert the benzaldehyde compound (III) obtained as the oxidation product and thereby to give the aminonitrile compound (II) may be generally carried out in a solvent, which may be any one so long as it does not adversely affect the reaction. Examples of the solvent include water, acetone, benzene, methanol, ethanol, dimethylformamide and mixtures thereof. As the ammonium salt for use in this reaction, ammonium chloride and bromide may be typically exemplified. The ammonium salt may be used alone but preferably used in combination with ammonia. As the salt of hydrocyanic acid, an alkali metal cyanide such as sodium or potassium cyanide may be frequently used. Instead of hydrocyanic acid, gaseous hydrogen cyanide may be introduced into the reaction system during the course of the reaction. The reaction temperature is not critical and the reaction even at ambient temperature usually gives a good yield.

The resultant aminonitrile compound (II) may be isolated and recovered from the reaction mixture by any conventional procedure. However, it may be directly (namely, without isolation) subjected to the hydrolysis as mentioned above for the production of the final, new compound (I) of this invention.

In an alternative way, the substituted benzaldehyde compound of the above formula (III) may be prepared by reducing an ester compound of the formula:

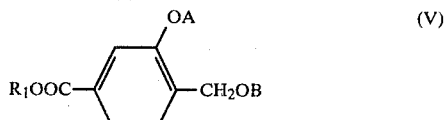

wherein A and B are as defined hereinbefore and R$_1$ represents an alkyl group, or an amide derivative thereof (preferably the amide derivative with a tertiary amine), under moderate, reducing conditions using a suitable reducing agent, for example, a methal hydride complex such as lithium aluminum hydride, sodium borohydride, lithium borohydride or sodium dihydro-bis-(2-methoxyethoxy) aluminate. The reduction is generally carried out in an inert solvent, for example, diethylether, dioxane or tetrahydrofuran.

Depending upon the reaction conditions employed, the alcohol compound (IV) may be produced from the reduction of the ester compound (V) with a metal complex, for example, sodium borohydride, lithium borohydride, lithium aluminum hydride or sodium dihydro-bis-(2-methoxyethoxy) aluminate. In this case, the reduction is carried out in an inert solvent including benzene, tetrahydrofuran and dioxane. The reaction temperature, though not critical, is usually ambient or an elevated temperature. In formula (V), $R_1$ is preferably a lower alkyl group such as methyl, ethyl, propyl or butyl group.

Further, ester compound of formula (V) may be prepared by reducing a hydroxyterephthalic acid alkyl ester of the above formula (VII) with, for example, sodium borohydride or lithium borohydride and then blocking the reduction product of the formula (VI) with a hydroxyl-protecting group which preferably enables simultaneous protection of the phenolic hydroxyl and the hydroxymethyl group, for example, isopropylidene group. The reduction and the protecting reaction may be conducted in a conventional manner. If the initial compound (VII), namely the hydroxyterephthalic acid alkyl ester is reduced under heating with a strong reducing agent, for example, lithium aluminum hydride or sodium dihydro-bis-(2-methoxyethoxy) aluminate, then both the ester groups of the compound (VII) can be reduced at once to yield a compound of the above formula (VI'). The blocking of the compound (VI') with a divalent hydroxyl-protecting group of blocking both the phenolic hydroxyl and the adjacent hydroxymethyl groups can directly lead to formation of the alcohol compound (IV) not via the compound (V).

Moreover, the novel compound (I), forphenicinol, of this invention may also be produced through a reduction of the aldehyde group of the known compound, forphenicine into the hydroxymethyl group by reacting with an appropriate reducing agent.

In a further aspect of this invention, therefore, there is provided a process for the production of the compound (I) which comprises reducing forphenicine of the structural formula:

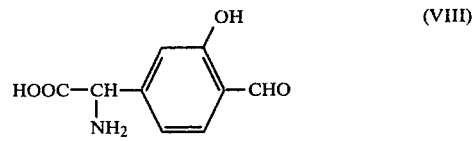
(VIII)

A preferred reducing agent to be used in the process is a metal hydride complex, for example, sodium borohydride or lithium borohydride. The reduction is generally carried out in a solvent. As the solvent there may be used any one in which forphenicine and the reducing agent both can be dissolved and which has no adverse influence on the reaction. Water is a typical example of the available solvents. The reaction may be effected at ambient temperature or at an elevated temperature.

As noted hereinabove, the compound (I) of this invention may form salts with different acids and bases. These salts can be derived from the compound (I) by any conventional method known per se.

In order to evaluate the immunopotentiating properties of the compound (I) of this invention, the effect of the compound (I) on cellular immunity (cell-mediated immunity) was tested according to a known Delayed-Type Hypersensitivity (D.T.H.) technique (see P. H. Lagrange, G. B. Mackaness and T. E. Mille, "J. Exp. Med", 139, 1529-1539 (1974)) using mice immunized with sheep red blood cells as antigen.

Thus, $10^8$ sheep red blood cells (SRBC) suspended in 0.05 ml of physiological saline were subcutaneously injected at the time of immunization to the right hind footpad of each dd/Y mouse under test (female, 6 weeks old) to establish delayed-type hypersensitivity. Simultaneously with the immunization, a varying dose of the compound (I) was intraperitoneally injected or orally administered into each test mouse. Four days later, $10^8$ sheep red blood cells were subcutantaneously injected into the left hind footpad of each test mouse for elicitation of the D.T.H. response. 24 hours after the elicitating injection, the thickness of the left hind footpad was measured to evaluate the degree of the swelling in the footpad. The degree of the swelling serves to estimate the cellular immunity involved. The test results obtained are set out in Table 1 below. In the Table, the swelling degree is expressed in terms of the values calculated by the equation:

$$\frac{\left(\begin{array}{c}\text{Thickness of the footpad of mouse}\\\text{treated with the subject compound}\end{array}\right)}{\left(\begin{array}{c}\text{Thickness of the footpad of mouse}\\\text{untreated}\end{array}\right)} \times 100$$

Table 1

| Dose of | Degree of swelling | |
|---|---|---|
| compound | i.p. injection | Oral administration |
| 100 μg/mouse | 131 | 166 |
| 10 μg/mouse | 148 | 191 |
| 1 μg/mouse | 159 | 133 |
| 0.1 μg/mouse | 183 | 139 |

The above results show that the new compound of the invention brings about an intensive potentiating effect on establishment of cellular immunity either by intraperitoneal injection or by oral administration of the compound at a wide range of dosages. This reveals that the new compound can be effectively used for immunotherapy and for treatment of immune diseases and disorders.

The compound (I) of the invention exhibits an $LD_{50}$ value of more than 500 mg/kg when intraperitoneally injected into mice.

According to a still further aspect of this invention, there is provided a process of potentiating the immune response in a living animal including man, which comprises administering orally or parenterally into the animal an effective amount of the compound of the above formula (I) or a pharmaceutically acceptable salt or hydrate thereof.

This invention also provides a pharmaceutical composition, useful as immunopotentiator, comprising as active ingredient the compound of the above formula (I) or a pharmaceutically acceptable salt or hydrate thereof or a salt of hydrate, in combination with a pharmaceutically acceptable carrier or adjuvant for the active ingredient.

The composition of the invention may be formulated for oral or parenteral administration. Compositions in the form of injectable solution may contain 0.1% to 10% by weight of forphenicinol as the active ingredient, and also one or more of a pH adjustor, buffer, stabilizer, excipient, local anesthetics and an additive for rendering the solutions isotonic. The injectable solutions may be prepared to be adapted for subcutaneous, intramuscular or intravenous injection by any conventional technique. If desired, the solutions may be lyophilized in a usual manner to prepare lyophilized injections.

Solid compositions for oral administration, which may be in the form of tablets, coated tablets, granules, powders and capsules, may contain excipients for the active ingredients and, if required, other additives including disintegrators, lubricants, colorants, sweetening agents and flavorings. The proportion of forphenicinol to the carrier usually may be at a ratio of from 1:1 to 1:100 by weight and may chosen appropriately depending on the form of the orally administerable formulation prepared.

Liquid compositions for oral administration, which may be in the form of syrups and dry syrups, may also contain sweetening agents, buffers, stabilizers, flavorings and the like.

Suppository formulations may contain excipients and, if necessary, surfactants in addition to the active ingredient.

The dosage of the compound (I) administered will, of course, depend on the mode of administration and the treatment desired. For men, the unit dosage generally comprises from 0.02 mg to 200 mg of the compound (I), which may be administered in divided doses one or more times per day.

This invention is further illustrated but not limited by the following Examples.

EXAMPLE 1

This Example illustrates the preparation of the compound having the formula:

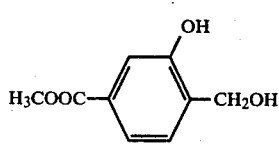

Into a three-necked flask of 300 ml capacity fitted with a cooling tube were placed 1577 mg of dimethyl hydroxyterephthalate of the formula

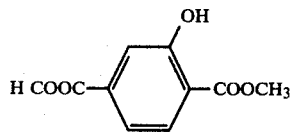

together with 50 ml of methanol. 5675 mg of sodium borohydride was slowly added to the contents of the flask under stirring, during which effervescence heat evolution and reflux began to take place. After completion of the addition over about 2 hours, the reaction mixture was refluxed for further one hour to complete the reduction. 100 ml of water was then added to the reaction solution, which was adjusted to pH 2 with 6 N hydrochloric acid, followed by addition of 50 ml of butanol. The methanol solvent was then distilled off under reduced pressure and the residue was extracted three times with 50 ml of butanol. The butanol extracts were combined together and washed with 20 ml of water. Removal of the butanol by evaporation under reduced pressure gave 1548 mg of a colorless powder. The powder was taken up in benzene and the solution was passed through a column of 100 ml of silica gel (Kieselgel, 60, 70–230 meshes, made by Merck Co.) which was charged as a suspension in benzene, for adsorption of the desired compound. The column was washed with 500 ml of a mixture of benzene-ethyl acetate (9:1 by volume) and then eluted with a mixture of benzene-ethyl acetate (4:1 by volume). The eluate was collected in fractions of each 15 g and fraction Nos. 35–65 containing the desired compound were combined together and evaporated under reduced pressure to remove the solvent, yielding 1224 mg of colorless crrstals. Recrystallization from a mixture of methanol-benzeneethylether gave 914 mg of the compound of formula (VI') as colorless crystals with a melting point of 104.5°–105° C.

I.R. spectrum:

$\nu_{max}^{KBr}$ (cm$^{-1}$): 3430, 3200, 2920, 1708, 1695, 1612, 1590, 1517, 1440, 1420, 1370, 1360, 1295, 1280, 1255, 1220, 1190, 1178, 1110, 1095, 1030, 978, 950, 923, 880, 872, 840, 805, 790, 756

N.M.R. spectrum (60 MHz, in deutero-methanol)

$\delta_{ppm}^{TMS}$:3.88 (3H, S), 4.72 (2H, S, overlap with the signal of deutero-water), 7.3–7.7 (3H)

EXAMPLE 2

This Example illustrates the preparation of the compound having the formula:

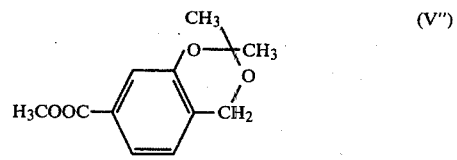

1224 mg of the compound (VI') obtained in Example 1 was suspended in 30 ml of dry benzene, to which were then added 5 ml of 2,2-dimethoxypropane and 50 ml of p-toluenesulfonic acid monohydrate to introduce isopropylidene group as the hydroxyl-protecting group. The resultant mixture was allowed to stand at room temperature for 3 hours to effect the reaction. The clear reaction solution was passed through a column of silica gel (the same one as described in Example 1). The column was then washed with benzene and the washings were combined with the effluent from the column. The combined solution (about 250 ml in total) was evaporated under reduced pressure to remove the solvent, leaving 1462 mg of a colorless oil. On standing at room temperature the oil was solidified into colorless crystals of the desired compound (V") having a melting point of 47.5°–48° C.

I.R. spectrum:

$\nu_{max}^{KBr}$ (cm$^{-1}$): 2990, 2950, 2860, 1712, 1620, 1580, 1505, 1430, 1378, 1360, 1310, 1283, 1255, 1240, 1220, 1140, 1120, 1093, 1052, 985, 953, 930, 920, 885, 845, 838, 820, 790, 760, 735

N.M.R. spectrum (60 MHz, in CDCl₃, with internal reference to TMS)

$\delta_{ppm}^{TMS}$: 1.53 (6H, s), 3.89 (3H, s), 4.88 (2H, s), 7.04 (1H, doublet-like), 7.52 (1H, singlet-like), 7.60 (1H, dd)

EXAMPLE 3

This example illustrates the preparation of the compound of the formula:

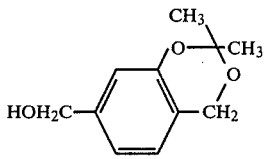 (IV″)

1460 mg of the compound (V″) obtained in Example 2 was dissolved in 20 ml of dry benzene. To the solution was added dropwise with ice cooling 2.8 ml of 70% sodium dihydro-bis(2-methoxyethoxy) aluminate (a reducing agent made by Wako Junyaku K.K.) solution in benzene and the mixture was allowed to stand at ambient temperature for 2 hours to effect the reduction. The reaction mixture was then ice-cooled and adjusted to pH 7 with 1 N hydrochloric acid. The white precipitate formed was filtered off, the filtrate was extracted with benzene and the extract was evaporated under reduced pressure to remove the benzene, affording 1213 mg of colorless crystals. Recrystallization from benzene-cyclohexane gave 928 mg of the desired compound (IV″) as colorless needles with a melting point of 73.5°–75.5° C.

I.R. spectrum $\nu_{max}^{KBr}$: 3350, 3250, 2955, 2875, 1623, 1580, 1510, 1455, 1430, 1375, 1355, 1300, 1285, 1263, 1235, 1205, 1160, 1142, 1115, 1065, 1053, 1020, 990, 980, 970, 935, 938, 920, 873, 851, 813, 798, 758, 730, 702, 668

N.M.R. spectrum (60 MHz, in CDCl₃)

δ $_{ppm}^{TMS}$: 1.53 (6H, s), 1.82 (1H, t), 4.62 (2H, d), 4.85 (2H, s), 6.8–7.0 (3H)

EXAMPLE 4

This Example illustrates the preparation of the compound of the formula:

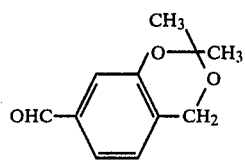 (III″)

250 mg of chromium trioxide was suspended in 10 ml of dry methylene chloride, to which was then added 240 mg of 3,5-dimethylpyrazol. The mixture was agitated at room temperature for 2 hours, followed by addition of a solution of the compound (IV″) from Example 3 in 2 ml of dry methylene chloride. The resultant mixture was allowed to stand at ambient temperature for 2 hours to effect the oxidation. Thereafter, 100 ml of ethyl ether was added to the reaction solution and the precipitate formed was filtered off and washed with ethyl ether. The filtrate and the washings were combined together and evaporated under reduced pressure to remove the solvent. The residue was taken up in benzene and the solution was passed through a column of 50 ml of silica gel (the same one as described in Example 1) which was charged while being suspended in benzene. The column was washed with 150 ml of benzene and then eluted with a mixed solvent of benzene-ethyl acetate (50:1 by volume). The eluate was collected in fractions of each 15 g and fraction Nos. 13–22 containing the desired compound was combined together and evaporated under reduced pressure to remove the solvent. There was thus obtained 164 mg of the desired compound (III″) as colorless viscous liquid.

I.R. spectrum:

$\nu_{max}^{KBr}$ (cm⁻¹): 2975, 2950, 2850, 2760, 1695, 1615, 1580, 1505, 1438, 1400, 1383, 1365, 1320, 1290, 1258, 1210, 1148, 1112, 1060, 1000, 985, 952, 880, 848, 830, 812, 775, 735, 705, 670

N.M.R. spectrum (60 MHz, in CDCl₃)

$\delta_{ppm}^{TMS}$: 1.55 (6H, s), 4.91 (2H, s), 7.15 (1H, d), 7.34 (1H, d), 7.47 (1H, dd), 9.91 (1H, s)

EXAMPLE 5

This example illustrates the preparation of the aminonitrile compound of the structure:

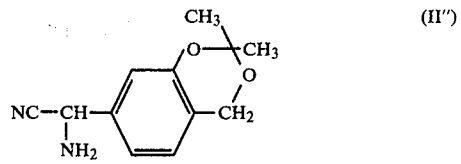 (II″)

216 mg of sodium cyanide was dissolved in 5 ml of concentrated aqueous ammonia (25–28%), to which were then added with ice-cooling under stirring 236 mg of ammonium chloride and a methanolic solution of 206 mg of the compound (III″) obtained in Example 4. The mixture was allowed to stand at room temperature for 4.5 hours to complete the reaction. Subsequently, the reaction solution was evaporated under reduced pressure to remove the ammonia and methanol, followed by dilution with 30 ml of water and extraction with butanol (3×10 ml). The extracts were combined together and evaporated to dryness under reduced pressure. The residue was taken up in methanol and the solution was dried in vacuo over silica gel (the same one as described in Example 1) and then suspended in benzene. The suspension was superposed on a column of 50 ml of silica gel (the same one as above) which was charged while being suspended in benzene. The column was washed with benzene and then eluted with a mixed solvent of benzene-ethyl acetate (4:1 by volume). The eluate was collected in fractions of each 15 g and fraction Nos. 14–35 containing the desired compound were combined together and evaporated under reduced pressure to remove the solvent. There was thus obtained 198 mg of the titled compound (II″).

I.R. spectrum:

$\nu_{max}^{KBr}$: 3400, 3320, 2980, 2950, 2870, 2220, 1623, 1585, 1505, 1435, 1388, 1380, 1363, 1315, 1288, 1258, 1200, 1142, 1120, 1055, 980, 950, 900, 870, 850, 820, 760, 735, 700

N.M.R. spectrum (60 MHz, in CDCl₃)

$\delta_{ppm}^{TMS}$: 1.53 (6H, s), 3.27 (2H, s, broad), 4.83 (2H, s), 4.88 (1H, s), 6.8–7.2 (3H)

The following Examples 6–8 illustrate the preparation of the final compound (forphenicinol) of the structural formula:

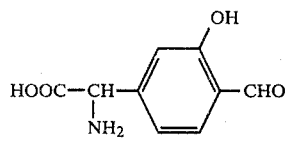

EXAMPLE 6

198 mg of the aminonitrile compound (II") obtained in Example 5 was dissolved in 5 ml of ethanol, and 3 ml of water and 2 g of barium hydroxide were added to the solution. The resultant mixture was refluxed for 5 hours to effect the hydrolysis. The reaction solution was then cooled to room temperature, diluted with water and adjusted to pH 2.0 with 1 N sulfuric acid, followed by reflux for further 30 minutes (for removal of the hydroxyl-protecting, isopropylidene group). After completion of the reaction, the reaction mixture was subjected to centrifugation (3000 revolutions per minute) for 10 minutes to remove the barium sulfate produced and the supernatant was concentrated by evaporation under reduced pressure. The concentrate was passed through a column of 10 ml of SP- Sephadex C-25 (H+form, made by Pharmacia Fine Chemicals Co., Sweden) to adsorb thereon the desired compound. The column was then eluted with water and the eluate was collected in fractions. Those fractions which contained the object compound were combined together and evaporated to dryness under reduced pressure to yield 89 mg of a pale yellow powder. The powder was crystallized from water to give 62 mg of forphenicinol, i.e. the new compound (I) as colorless crystals. This compound has a melting point of 200° C. but gradually decomposes above 200° C. to discolor into brown.

I.R. spectrum $v_{max}^{KBr}$: 3450, 3030, 2950, 2920, 2875, 2710, 2610, 2320, 2080, 1640, 1620, 1592, 1530, 1495, 1440, 1410, 1380, 1350, 1320, 1303, 1258, 1200, 1165, 1135, 1120, 1038, 980, 970, 940, 910, 872, 830, 780, 760, 738, 675, N.M.R. spectrum $\delta_{ppm}^{ext.TMS}$: 5.12 (2H, s), 5.18 (1H, s), 735–7.55 (2H), 7.82 (1H, d)

EXAMPLE 7

108 mg of sodium cyanide was dissolved in 3 ml of conc. aqueous ammonia (25–28% by weight) and the solution was admixed with ice-cooling under agitation with 118 mg of ammonium chloride and a methanolic solution of 170 mg of the compound (III") obtained in Example 4. The admixture was allowed to stand at ambient temperature for 15 hours to effect the reaction. The reaction solution was evaporated to remove the ammonia and methanol, then diluted with 30 ml of water and extracted with butanol (3×10 ml). The extracts were combined together, washed with 5 ml of water and then evaporated under reduced pressure to remove the butanol. The residue comprising the aminonitrile compound (II") was taken up in 5 ml of methanol, to which were then added 2 g of barium hydroxide and 3 ml of water. The mixture was heated under reflux for 5 hours to accomplish the hydrolysis. Thereafter, the reaction mixture was cooled to room temperature, diluted with water and adjusted to pH 2.0 with 1 N sulfuric acid, followed by heating at 100° C. for 30 minutes (for removal of the isopropylidene group). The resulting reaction mixture was subjected to centrifugation (3000 revoutions per minute) for 10 minutes to remove the barium sulfate produced and the supernatant was concentrated by evaporation under reduced pressure. The concentrate was passed through a column of 10 ml of SP-Sephadex C-25 (as indicated in Example 6) and the column was eluted with water. The eluate was collected in fractions of each 7 g. Fraction Nos. 8–25 which contained the desired compound were combined together, concentrated under reduced pressure and dried in vacuo to afford 63 mg of pale yellow crystals. The physico-chemical properties of the product were identical to those of the product obtained in Example 6.

EXAMPLE 8

587 mg of forphenicine was suspended in 25 ml of water and 120 mg of sodium borohydride was slowly added in small portions to the suspension under vigorous stirring. After completion of the addition, the reduction took place at room temperature for 10 minutes. The reaction solution was then adjusted to pH 2 with 1 N hydrochloric acid and passed through a column (3.5×28 cm) of SP-Sephadex C-25 (as indicated in Example 6) to adsorb thereon the desired compound. The column was eluted with water and the eluate was collected in fractions of each 18 g. Fraction Nos. 215–310 which contained the object compound (I) were combined together and concentrated to a volume of 5 ml by evaporation under reduced pressure. The precipitated colorless crystals were filtered off and dried in vacuo to yield 398 mg of the forphenicinol (I).

Elemental Analysis: Found: C: 54.58, H: 5.61, N: 7.22: Calcd. for $C_9H_{11}NO_4$: C: 54.82, H: 5.62, N: 7.10.

The following Examples 9–10 illustrate the formulation of the pharmaceutical compositions comprising the compound (I) as active ingredient and which can be suitably used as immunopotentiator for animals and men.

EXAMPLE 9

10 g of the compound (I) was dissolved in distilled water to give 1000 ml of the solution, which was sterilized in a conventional manner. The sterilized solution was charged in 2 ml portions into vials and lyophilized. The formulation so obtained is diluted with distilled water to give an injectable solution before use.

EXAMPLE 10

One part of the compound (I), 200 parts of lactose and 50 parts of corn starch were mixed together and the mixture was granulated with addition of ethanol, dried and then screened in a usuall manner. The granules obtained were admixed with 0.5% magnesium stearate as lubricant and the admixture was shaped into tablets of each 3.6 mg weight by a conventional technique.

EXAMPLE 11

One part of the compound (I) was thoroughly mixed with 900 parts of lactose and the mixture was screened with a 50 mesh sieve to form powders.

What we claim is:

1. A compound of the formula:

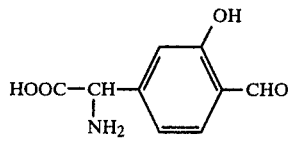

and its pharmaceutically acceptable salts and hydrates and pharmaceutically acceptable salts of the hydrates.

2. A pharmaceutical composition, useful as immunopotentiator, comprising as active ingredient the compound of formula (I) as described in claim 1 or a pharmaceutically acceptable salt or hydrate thereof, in combination with a pharmaceutically acceptable carrier or adjuvant.

3. A process of potentiating the immune response in a living animal including man, which comprises administering orally or parenterally into the animal an effective amount of the compound of formula (I) as described in claim 1 or a pharmaceutically acceptable salt or hydrate thereof.

4. A process according to claim 3 in which the compound (I) is administered into man at a unit dosage of 0.02 to 200 mg one or more times per day.

* * * * *